US012685485B1

(12) United States Patent     (10) Patent No.:   US 12,685,485 B1

Oliver et al.     (45) Date of Patent:    Jul. 21, 2026

(54) SYSTEMS, DEVICES, AND/OR METHODS FOR MANAGING VEIN LOCATION

(71) Applicants: Sheila Kaitlyn Oliver, Mountain View, HI (US); Jack Russell Brauher, Mountain View, HI (US)

(72) Inventors: Sheila Kaitlyn Oliver, Mountain View, HI (US); Jack Russell Brauher, Mountain View, HI (US)

( * ) Notice: Subject to any disclaimer, the term of this patent is extended or adjusted under 35 U.S.C. 154(b) by 0 days.

(21) Appl. No.: 18/072,408

(22) Filed: Nov. 30, 2022

Related U.S. Application Data

(60) Provisional application No. 63/284,163, filed on Nov. 30, 2021.

(51) Int. Cl.
    *A61B 5/00*       (2006.01)

(52) U.S. Cl.
    CPC ..................................... *A61B 5/489* (2013.01)

(58) Field of Classification Search
    CPC ....................................................... A61B 5/489
    See application file for complete search history.

(56) References Cited

U.S. PATENT DOCUMENTS

2011/0245685 A1\* 10/2011 Murata .................. A61B 5/489
                                                   600/476
2020/0297352 A1\* 9/2020 Altrichter ............ A61B 17/135

\* cited by examiner

*Primary Examiner* — Mark D Remaly

(74) *Attorney, Agent, or Firm* — Bhasin Law, a PC

(57) ABSTRACT

Certain exemplary embodiments provide a device comprising a band comprising a magnetic material. The magnetic material can comprise Neodymium (Nd—Fe—B) and/or Samarium Cobalt (SmCo). Certain exemplary embodiments provide a method comprising utilizing a magnetic band to restrain motion of a vein in a human, wherein a blood sample is taken from the vein or a medication is injected into the vein.

9 Claims, 5 Drawing Sheets

5000

1000

2000

3000

4000

Fabricate magnetic band          4100

Don magnetic band          4200

Locate vein          4300

Draw blood from vein          4400

Inject medication in vein          4500

Apply tourniquet to vein          4600

5000

SYSTEMS, DEVICES, AND/OR METHODS FOR MANAGING VEIN LOCATION

CROSS-REFERENCES TO RELATED APPLICATIONS

This application claims priority to, and incorporates by reference herein in its entirety, U.S. Provisional Patent Application Ser. No. 63/284,163, filed Nov. 30, 2021.

BRIEF DESCRIPTION OF THE DRAWINGS

A wide variety of potential practical and useful embodiments will be more readily understood through the following detailed description of certain exemplary embodiments, with reference to the accompanying exemplary drawings in which.

DETAILED DESCRIPTION

Certain exemplary embodiments provide a device comprising a band comprising a magnetic material. The magnetic material can comprise Neodymium (Nd—Fe—B) and/or Samarium Cobalt (SmCo). Certain exemplary embodiments provide a method comprising utilizing a magnetic band to restrain motion of a vein in a human, wherein a blood sample is taken from the vein or a medication is injected into the vein.

Certain exemplary embodiments provide a band that is wearable by a human (for example, a band worn on the wrist of a user) that allows blood veins to be located and restrained from motion such that blood can be drawn from the human more easily and/or more effectively.

Empirical observations have revealed that blood flow and vein position can be changed and/or maintained by application of a magnetic field. When a magnetic field is applied, veins can be easier to see and/or easier to insert a needle in for drawing blood and/or injecting medications. Magnetic fields can restrain motion of a vein once skin is depressed in order to cause a needle to enter the vein. Via restraint of motion by a magnetic field, insertion of a needle can be easier and/or fewer unsuccessful attempts to insert the needle can be possible.

At least one study has shown a correlation between an application of magnetic fields to blood vessel size. "Rotating magnetic field delays human umbilical vein endothelial cell aging and prolongs the lifespan of *Caenorhabditis elegans*", Xu J, Liu K, Chen T, Zhan T, Ouyang Z, Wang Y, Liu W, Zhang X, Sun Y, Xu G, Wang X, Aging (Albany NY). 2019 Nov. 22; 11 (22):10385-10408. doi: 10.18632/aging. 102466. Epub 2019 Nov. 22. PMID: 31757933; PMCID: PMC6914427. Applicant hereby incorporates the article "Rotating magnetic field delays human umbilical vein endothelial cell aging and prolongs the lifespan of *Caenorhabditis elegans*" by reference in its entirety.

When a magnetic field is applied, veins can be easier to see and/or easier to position a tourniquet to restrict blood flow.

Oxygenated hemoglobin molecules aren't attracted to a strong magnet field because such molecules are diamagnetic. This means oxygenated hemoglobin molecules are weakly repelled by a magnetic field due to a lack of unpaired electrons. Hemoglobin molecules that haven't been oxygenated on the other hand, have four unpaired electrons, making them slightly paramagnetic, or weakly attracted to a magnetic field. Because most of the blood in human bodies is made up of water (which is also diamagnetic) and oxygenated hemoglobin, human blood is, overall, diamagnetic, and therefore subtly repelled by magnetic fields. This property can be utilized for improved devices, systems, and/or methods for drawing blood and/or injecting medications.

Figure 1:
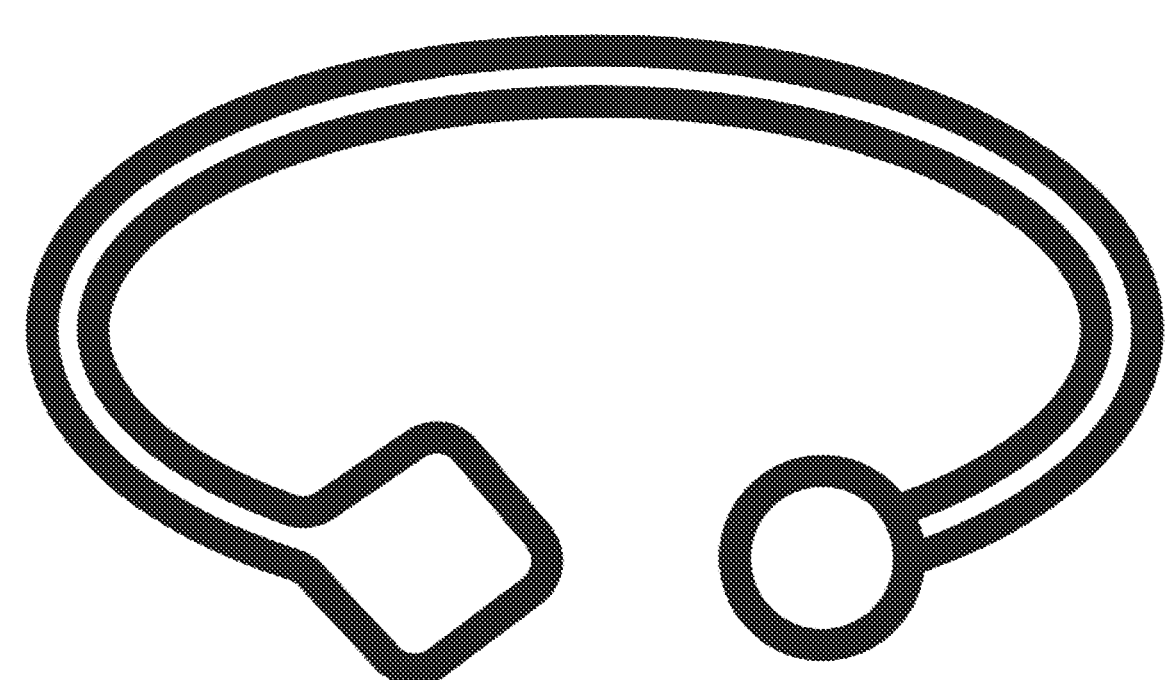
FIG. 1 is a perspective view of an exemplary embodiment of a band 1000.

FIG. 1 is a perspective view of an exemplary embodiment of a band 1000, which illustrates an open-ended band with shaped ends. Other band shapes are possible. For example, different end shapes can be used. In addition, any cross-sectional shape can be utilized. The illustrated embodiment has a substantially circular cross-section. Other embodiments can have a beveled or other cross-section. Band 1000 comprises a magnetic material such as a rare earth magnet material.

Figure 2:
FIG. 2 is a plan view of an exemplary embodiment of a band 2000.

FIG. 2 is a plan view of an exemplary embodiment of a band 2000, which illustrates a coupled set of magnetic links. Certain users might prefer the aesthetics of band 2000 relative to other possible appearances.

Figure 3:
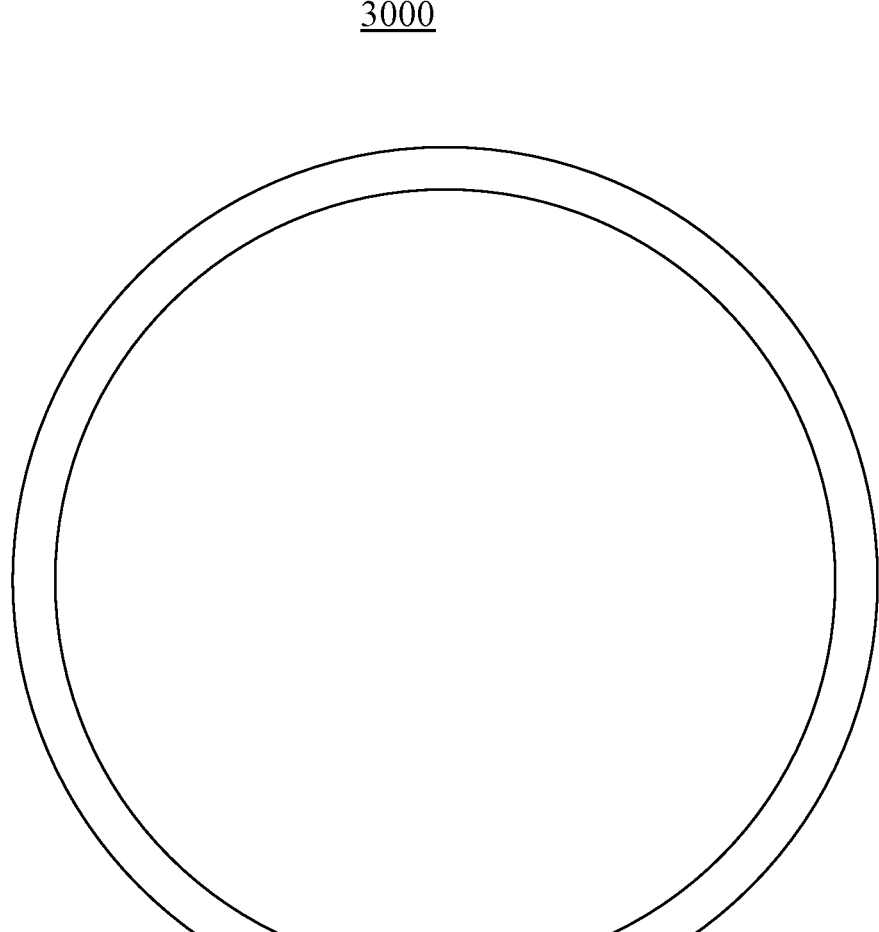
FIG. 3 is a plan view of an exemplary embodiment of a band 3000.

FIG. 3 is a plan view of an exemplary embodiment of a band 3000, which illustrates an annular shape.

Certain exemplary embodiments utilize rare earth magnets (e.g., Neodymium (Nd—Fe—B) and/or Samarium Cobalt (SmCo)). Certain exemplary embodiments can be relatively narrow in size. For example, certain exemplary magnetic bands are approximately three inches long and having a width that approximates a width of a pencil.

Magnetic bands can hold veins in a particular location while blood specimens are taken and/or medications are injected.

Certain exemplary embodiments comprise two magnets in a cuff.

Certain exemplary embodiments can be snapped onto an arm of a user prior to an injection into a vein or a needle placed into the vein to withdraw blood.

Certain exemplary embodiments can be beveled and press human skin inward when worn.

Certain exemplary embodiments comprise a rigid polymer such as Kevlar (Kevlar is a registered trademark of DuPont Safety & Construction, Inc. of Wilmington Delaware) or a like material, a non-magnetic metal such as aluminum, and/or hook and loop fasteners, etc.

Certain exemplary embodiments can utilize an elastic material (e.g., an elastomer) and/or can be adjustable in size. Thereby users with wrist or arms of varying sizes can utilize a given band.

In certain exemplary embodiments, users can wear magnetic bands for approximately 10 seconds prior to acting on a vein.

Certain exemplary embodiments can be effectively utilized with stainless steel needles, which stainless steel needles are non-magnetic.

Figure 4:
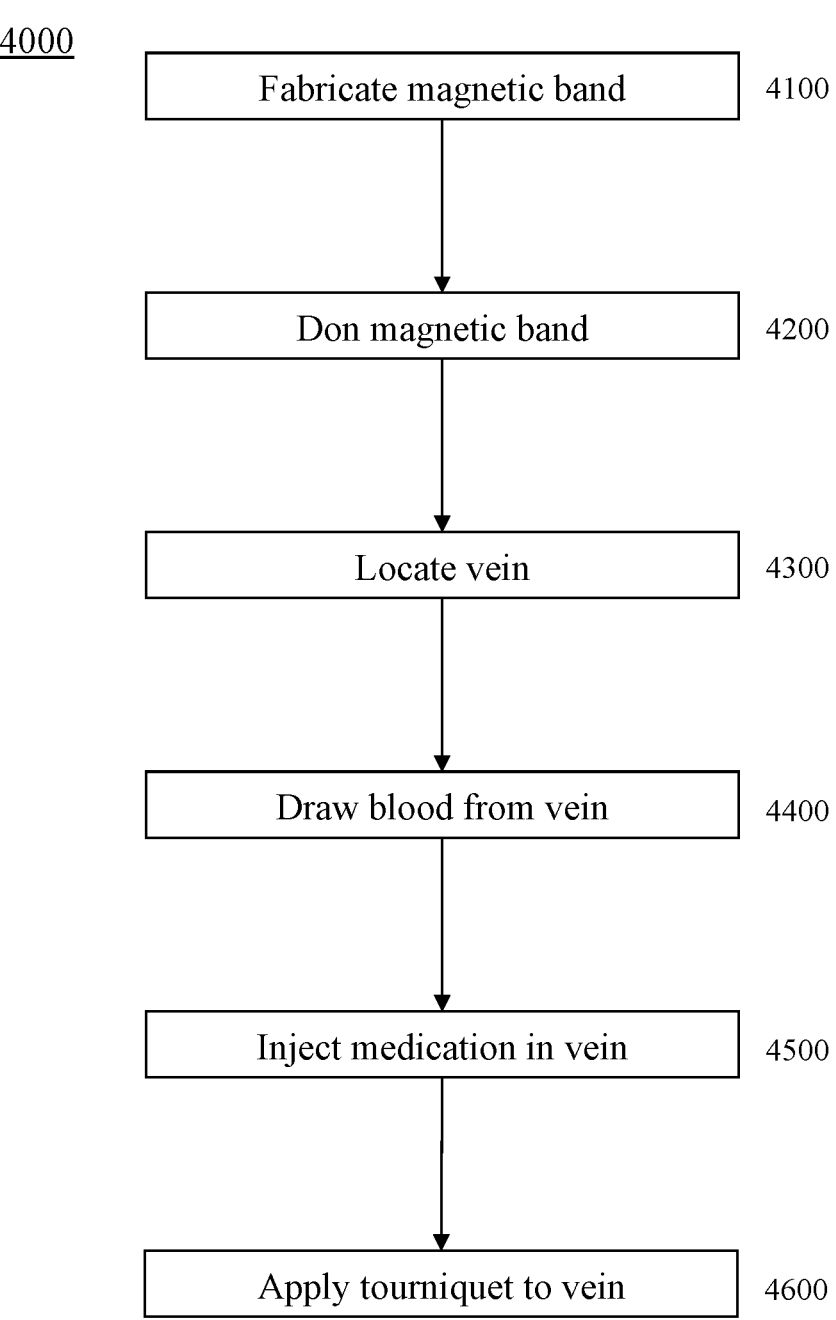
FIG. 4 is a flowchart of an exemplary embodiment of a method 4000.

FIG. 4 is a flowchart of an exemplary embodiment of a method 4000. At activity 4100, a magnetic band can be fabricated. At activity 4200, a user can don the magnetic band. At activity 4300, a vein can be located while the user is wearing the magnetic band. At activity 4400, blood can be drawn from the vein. At activity 4500, a medication can be injected into the vein. At activity 4600, a tourniquet can be applied to the vein.

Figure 5:
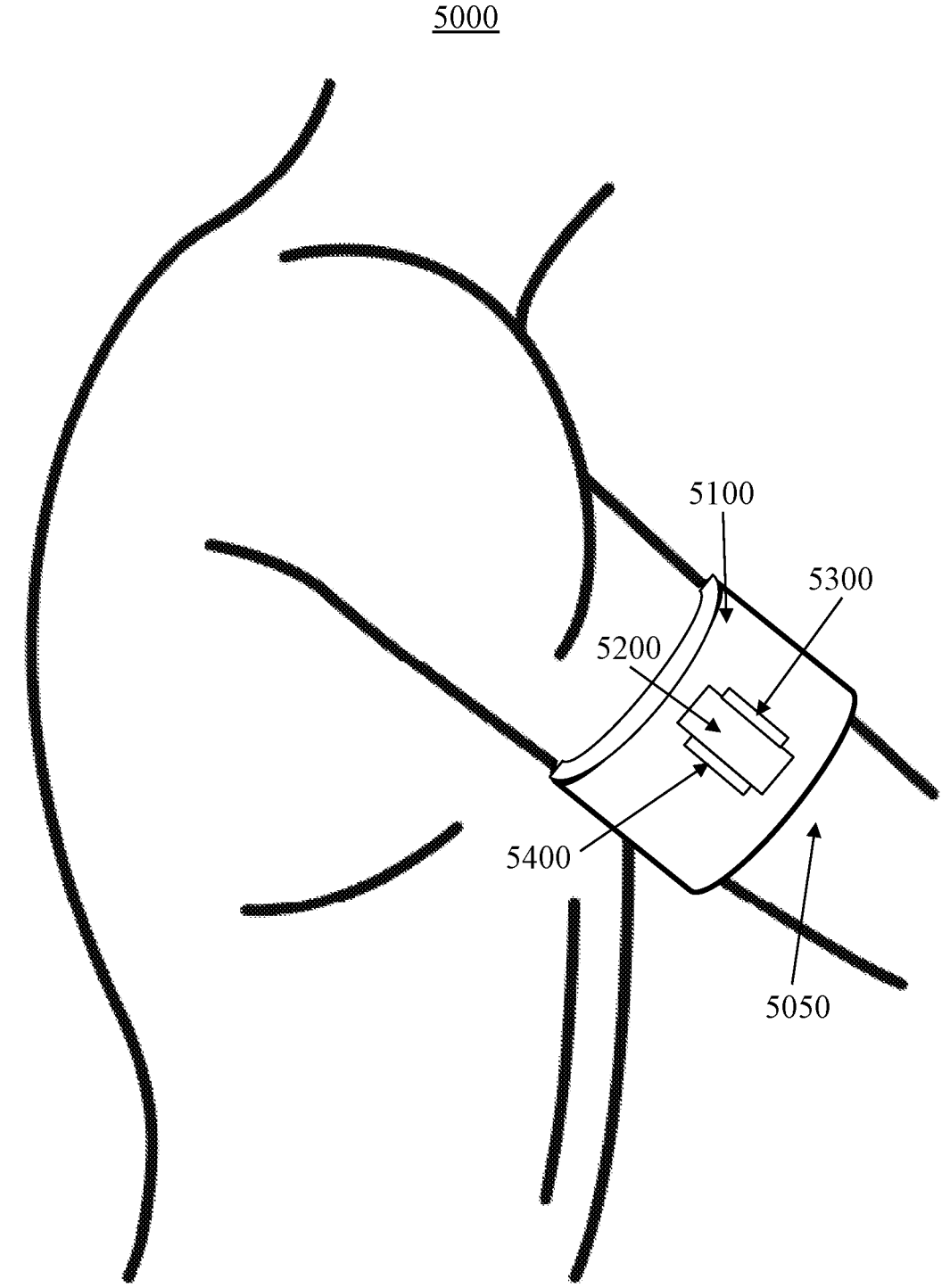
FIG. 5 is a perspective view of an exemplary embodiment of a system 5000.

FIG. 5 is a perspective view of an exemplary embodiment of a system 5000, which comprises a cuff 5100 that is coupled to a human forearm 5050. Cuff 5100 defines an aperture 5200. A user can insert a needle into human forearm 5050 via aperture 5200. Cuff 5100 comprises a first magnet 5300 and a second magnet 5400. First magnet 5300 and second magnet 5400 create tension on one or more veins in human forearm 5050. In certain exemplary embodiments, first magnet 5300 and second magnet 5400 are oriented with like magnet poles facing one another across aperture 5200 to generate a repulsive magnetic field extending between first magnet 5300 and second magnet 5400 and through aperture 5200 into soft tissue of human forearm 5050, thereby creating tension on one or more veins in human forearm 5050.

Materials utilized for cuff 5100 can comprise copper, aluminum, brass, and/or stainless steel, etc.

In certain exemplary embodiments, Kevlar (Kevlar is a registered trademark of E. I. Du Pont De Nemours and Company of Wilmington, DE) or similar material can be used. Certain exemplary embodiments stick to skin of a user via an adhesive.

In certain exemplary embodiments, magnets can be wrapped with copper bands etc. and/or copper can be incorporated within specifically manufactured magnets, which can increase a strength of a magnetic field with a charging effect. Certain exemplary embodiments can be tested via instrumentation and experiments to verify performance. Certain exemplary embodiments can be made with a fastening apparatus or can be pulled on the user as a cuff. Certain exemplary embodiments can utilize hook and loop fasteners. To couple cuff 5100 to human forearm 5050.

Definitions

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.

activity—an action, act, step, and/or process or portion thereof.

adapted to—made suitable or fit for a specific use or situation.

adapter—a device used to effect operative compatibility between different parts of one or more pieces of an apparatus or system.

arm—an upper human limb.

and/or—either in conjunction with or in alternative to.

apparatus—an appliance or device for a particular purpose.

aperture—an opening in something.

band—a circle of material.

blood—a fluid that circulates in a heart, arteries, capillaries, and veins of a human carrying nourishment and oxygen to and bringing away waste products from all parts of a body of the human.

can—is capable of, in at least some embodiments.

cause—to bring about.

change—to make different.

comprising—including but not limited to.

configure—to make suitable or fit for a specific use or situation.

connect—to join or fasten together.

constructed to—made to and/or designed to.

coupleable—capable of being joined, connected, and/or linked together.

coupling—linking in some fashion.

define—to establish the outline, form, or structure of.

device—a machine, manufacture, and/or collection thereof.

don—to wear.

human—a member of the species *Homo sapiens*.

inject—to introduce into something forcefully.

install—to connect or set in position and prepare for use.

Kevlar—Poly-paraphenylene terephthalamide, which is a strong, heat-resistant synthetic fiber, related to other aramids magnetic material—a substance or object that produces a magnetic field.

may—is allowed and/or permitted to, in at least some embodiments.

medication—a substance used in treating disease or relieving pain.

method—a process, procedure, and/or collection of related activities for accomplishing something.

motion—a process via which something changes position from one location to another.

plurality—the state of being plural and/or more than one.

predetermined—established in advance.

provide—to furnish, supply, give, and/or make available.

receive—to get, take, acquire, and/or obtain.

repeatedly—again and again; repetitively.

request—to express a desire for and/or ask for.

restrain—to limit motion of something.

sample—(n) a representative part from a larger whole; (v) the act of extracting a representative part from a larger whole.

set—a related plurality.

store—to place, hold, and/or retain.

substantially—to a great extent or degree.

support—to bear the weight of, especially from below.

system—a collection of mechanisms, devices, machines, articles of manufacture, processes, data, and/or instructions, the collection designed to perform one or more specific functions.

take—to extract.

tourniquet—a device constructed for stopping the flow of blood through a vein or artery, typically by compressing a limb with a cord or tight bandage.

transmit—to send, provide, furnish, and/or supply.

utilize—to put to use.

vein—any of a plurality of tubular branching vessels that carry blood from capillaries toward a heart of a human.

via—by way of and/or utilizing.

wearer—a human that dons something.

Note

Still other substantially and specifically practical and useful embodiments will become readily apparent to those skilled in this art from reading the above-recited and/or herein-included detailed description and/or drawings of certain exemplary embodiments. It should be understood that numerous variations, modifications, and additional embodiments are possible, and accordingly, all such variations, modifications, and embodiments are to be regarded as being within the scope of this application.

Thus, regardless of the content of any portion (e.g., title, field, background, summary, description, abstract, drawing figure, etc.) of this application, unless clearly specified to the contrary, such as via explicit definition, assertion, or argument, with respect to any claim, whether of this application and/or any claim of any application claiming priority hereto, and whether originally presented or otherwise:

> there is no requirement for the inclusion of any particular described or illustrated characteristic, function, activity, or element, any particular sequence of activities, or any particular interrelationship of elements;
>
> no characteristic, function, activity, or element is "essential";
>
> any elements can be integrated, segregated, and/or duplicated;
>
> any activity can be repeated, any activity can be performed by multiple entities, and/or any activity can be performed in multiple jurisdictions; and
>
> any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

When any claim element is followed by a drawing element number, that drawing element number is exemplary and non-limiting on claim scope. No claim of this application is intended to invoke paragraph six of 35 USC 112 unless the precise phrase "means for" is followed by a gerund.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such material is specifically not incorporated by reference herein.

Accordingly, every portion (e.g., title, field, background, summary, description, abstract, drawing figure, etc.) of this application, other than the claims themselves, is to be regarded as illustrative in nature, and not as restrictive, and the scope of subject matter protected by any patent that issues based on this application is defined only by the claims of that patent.

What is claimed is:

1. A device, comprising:
   an open-ended band configured as a cuff to couple to a forearm of a user, the cuff comprising a first magnet and a second magnet, the second magnet being spaced apart from the first magnet along a length of the cuff;
   an aperture positioned between the first magnet and the second magnet, the aperture providing an opening for insertion of a needle into a vein of the user;
   wherein the first magnet and the second magnet are oriented with like magnet poles facing one another across the aperture to generate a repulsive magnetic field extending between the first magnet and the second magnet and through the aperture into soft tissue of the forearm;
   wherein the magnetic field applies a magnetic force to diamagnetic blood within the vein positioned beneath the aperture, the magnetic force generating a tensioning effect on the vein that stabilize blood flow
   within the vein for withdrawal of the blood sample.

2. The device of claim 1, wherein:
   the magnetic material comprises Neodymium (Nd—Fe—B).

3. The device of claim 1, wherein:
   the magnetic material comprises Samarium Cobalt (SmCo).

4. The device of claim 1, wherein the device is a wearable device.

5. The device of claim 4, wherein the device is worn on a wrist of the user.

6. The device of claim 1, wherein the device allow a user to locate and stabilize the vein.

7. The device of claim 1, wherein the device is open-ended band with shaped ends.

8. The device of claim 1, wherein the first and second magnets are an earth magnetic material.

9. The device of claim 1, wherein the band holds the vein in a particular position for the user to inject a medication into the vein.

* * * * *